(12) United States Patent
Beckert et al.

(10) Patent No.: US 8,708,990 B2
(45) Date of Patent: Apr. 29, 2014

(54) ABSORBENT INCONTINENCE ARTICLE WITH IMPROVED CLOSURE SYSTEM

(71) Applicant: Paul Hartmann AG, Heidenheim (DE)

(72) Inventors: Susanne Beckert, Ulm (DE); Rüediger Kesselmeier, Herbrechtingen (DE)

(73) Assignee: Paul Hartmann AG, Heidenheim (DE)

( * ) Notice: Subject to any disclaimer, the term of this patent is extended or adjusted under 35 U.S.C. 154(b) by 0 days.

(21) Appl. No.: 13/861,341

(22) Filed: Apr. 11, 2013

(65) Prior Publication Data

US 2013/0237942 A1 Sep. 12, 2013

Related U.S. Application Data

(63) Continuation of application No. 13/404,019, filed on Feb. 24, 2012, which is a continuation of application No. 12/446,586, filed as application No. PCT/EP2007/009030 on Oct. 18, 2007, now Pat. No. 8,152,788.

(30) Foreign Application Priority Data

Oct. 27, 2006 (EP) .................................... 06022450

(51) Int. Cl.
*A61F 13/15* (2006.01)

(52) U.S. Cl.
USPC ............ 604/386; 604/387; 604/389; 604/391

(58) Field of Classification Search
USPC ............... 604/385.24, 385.26, 385.28, 385.3, 604/385.03, 367, 386, 387, 389, 391
See application file for complete search history.

(56) References Cited

U.S. PATENT DOCUMENTS

| 4,084,592 | A | 4/1978 | Tritsch |
| 4,663,220 | A | 5/1987 | Wisneski et al. |

(Continued)

FOREIGN PATENT DOCUMENTS

| DE | 10 2004 021353 | 11/2005 |
| DE | 10 2004 042405 | 3/2006 |

(Continued)

OTHER PUBLICATIONS

Petition for Inter Partes Review of U.S. Patent No. 8,152,788 Patent filed on Feb. 28, 2013, 65 pages, IPR2013-00173.

(Continued)

*Primary Examiner* — Jacqueline F. Stephens
(74) *Attorney, Agent, or Firm* — Proskauer Rose LLP

(57) ABSTRACT

The invention relates to an absorbent incontinence diaper (2) with a rear area (8), a front area (6) and a crotch area (12) lying between these, and with first and second side edges (5), and with a main part (4) having an inner face directed towards the body and an outer face directed away from the body during use of the diaper, the main part (4) comprising an absorption body (14) and a backsheet (10) on the side of the absorption body (14) directed away from the body, the absorption body (14) having a smaller width than the backsheet (10), and with side parts (16, 17) joined to the first and second side edges (5), the side parts (16, 17) having an inner face and an outer face, and the side parts (17) in the rear area having closure means (32) with mechanical closure aids (31). To correctly secure the diaper on the body of a user, the mechanical closure means (31) can be secured detachably at least in regions both on the outer face of the main part (4) and also on the outer face of the side parts (16) in the front area (6). The retaining forces between the mechanical closure means (31) and the outer face of the main part are lower than the retaining forces between the mechanical closure means (31) and the outer face of the side parts (16) in the front area (6).

21 Claims, 9 Drawing Sheets

(56) References Cited

U.S. PATENT DOCUMENTS

| | | |
|---|---|---|
| 5,246,431 A | 9/1993 | Minetola et al. |
| 5,549,592 A | 8/1996 | Fries et al. |
| 5,549,777 A | 8/1996 | Langdon et al. |
| 5,628,737 A | 5/1997 | Dobrin et al. |
| 5,685,873 A | 11/1997 | Bruemmer |
| 5,897,545 A | 4/1999 | Kline et al. |
| 5,904,793 A | 5/1999 | Gorman et al. |
| 6,218,593 B1 | 4/2001 | Torimae et al. |
| 6,332,250 B1 | 12/2001 | Igaue et al. |
| 6,402,730 B1 | 6/2002 | Malowaniec |
| 6,461,343 B1 | 10/2002 | Schaefer et al. |
| 6,524,294 B1 | 2/2003 | Hilston et al. |
| 6,548,147 B1 | 4/2003 | Raidel et al. |
| 6,582,543 B1 | 6/2003 | Nilsson et al. |
| 6,626,881 B2 | 9/2003 | Shingu et al. |
| 6,701,580 B1 | 3/2004 | Bandyopadhyay |
| 6,840,930 B1 | 1/2005 | Miyamoto et al. |
| 6,878,223 B2 | 4/2005 | Kuen et al. |
| 6,936,129 B2 | 8/2005 | Karami et al. |
| 7,482,505 B2 | 1/2009 | Stupperich et al. |
| 8,152,788 B2 | 4/2012 | Beckert et al. |
| 8,162,913 B2 | 4/2012 | Goates et al. |
| 8,216,414 B2 | 7/2012 | Hornung et al. |
| 2003/0119404 A1 | 6/2003 | Belau et al. |
| 2003/0125705 A1 | 7/2003 | Ruman et al. |
| 2005/0003143 A1 | 1/2005 | Ducauchuis et al. |
| 2005/0191460 A1 | 9/2005 | Belau |
| 2005/0256494 A1 | 11/2005 | Datta |
| 2005/0256496 A1 | 11/2005 | Benning et al. |
| 2005/0261647 A1 | 11/2005 | Karami et al. |
| 2005/0261650 A1 | 11/2005 | Damaghi et al. |
| 2006/0058772 A1 | 3/2006 | Karami |
| 2006/0247596 A1 | 11/2006 | Van Dyke |
| 2006/0282053 A1 | 12/2006 | Rohrl |
| 2007/0254158 A1 | 11/2007 | Bormann et al. |
| 2008/0026178 A1 | 1/2008 | Stupperich et al. |
| 2008/0208152 A1 | 8/2008 | Eckstein et al. |
| 2009/0069776 A1 | 3/2009 | Utsunomiya et al. |

FOREIGN PATENT DOCUMENTS

| | | |
|---|---|---|
| DE | 10 2004 053469 | 5/2006 |
| EP | 0 800 808 | 10/1997 |
| EP | 0 882 828 | 12/1998 |
| EP | 1 048 236 | 11/2000 |
| EP | 1 655 006 B1 | 5/2006 |
| EP | 1 915 977 | 4/2008 |
| IT | 20030113 A1 | 5/2003 |
| JP | 09-173382 | 7/1997 |
| JP | 09-509901 | 10/1997 |
| JP | 2000-270908 | 10/2000 |
| JP | 2000-513644 | 10/2000 |
| JP | 2005-514530 | 5/2005 |
| JP | 2005-537039 | 12/2005 |
| JP | 2006-508870 | 3/2006 |
| JP | 2006-187646 | 7/2006 |
| JP | 2007-268220 | 10/2007 |
| WO | 99/37263 | 7/1999 |
| WO | 03/082167 | 10/2003 |
| WO | 2004/105668 | 12/2004 |
| WO | 2005/102241 | 11/2005 |
| WO | 2006/048173 | 5/2006 |
| WO | 2007/001815 | 1/2007 |
| WO | 2008/049546 | 5/2008 |

OTHER PUBLICATIONS

IPR2013-000173, Exhibit 1004 submitted with Petition (Feb. 28, 2013), File History of U.S. Patent No. 8,152,788 to Beckert et al.

IPR2013-000173, Exhibit 1018 submitted with Petition (Feb. 28, 2013), Declaration under 35 U.S.C. §§ 311-319 and 37 C.F.R. § 42 of Arrigo D. Jezzi Supporting the Invalidity of U.S. Patent No. 8,152,788.

*Medline Industries, Inc.* v. *Paul Hartmann AG*, United States District Court Northern District of Illinois, Case No. 1:13-cv-01623 Complaint for Declaratory Relief filed Mar. 1, 2013; 27 pages.

*Medline Industries, Inc.* v. *Paul Hartmann AG*, United States District Court Northern District of Illinois, Civil Docket for Case No. 1:13-cv-01623, generated date Apr. 11, 2013, 2 pages.

EPO Office Action in EP Appl. No. 07819098 citing Van Gompel, Aug. 27, 2013, 5 pages (in German).

Patent Owner's Response with Exhibits, filed in IPR2013-00173, Sep. 19, 2013, 490 pages.

Declaration of Andrew Urban III, with Exhibits, Sep. 19, 2013, 63 pages.

Videotaped Deposition of Andrew Urban III, with Exhibits, Nov. 7, 2013, 472 pages.

EPO Office Action in EP Appl. No. 06022450 citing Van Gompel, Aug. 27, 2013, 7 pages (in German).

*Medline Industries, Inc.* v. *Paul Hartmann AG*, United States District Court Northern District of Illinois, Civil Docket for Case No. 1:13-cv-01623, generated date Nov. 19, 2013, 2 pages.

U.S. Appl. No. 12/446,586, filed Apr. 22, 2009, Beckert et al.
U.S. Appl. No. 13/404,019, filed Feb. 24, 2012, Beckert et al.
U.S. Appl. No. 12/798,242, filed Mar. 13, 2013, Beckert et al.
U.S. Appl. No. 13/861,341, filed Apr. 11, 2013, Beckert et al.
IPR2013-00173, filed Feb. 28, 2013, Beckert et al.
IPR2013-00173, Decision: Institution of Inter Partes Review under 37 C.F.R. § 42.108 (issued: Jun. 20, 2013 by the Patent Trial and Appeal Board), Paper 17, relating to U.S. Patent No. 8,152,788 to Beckert et al.

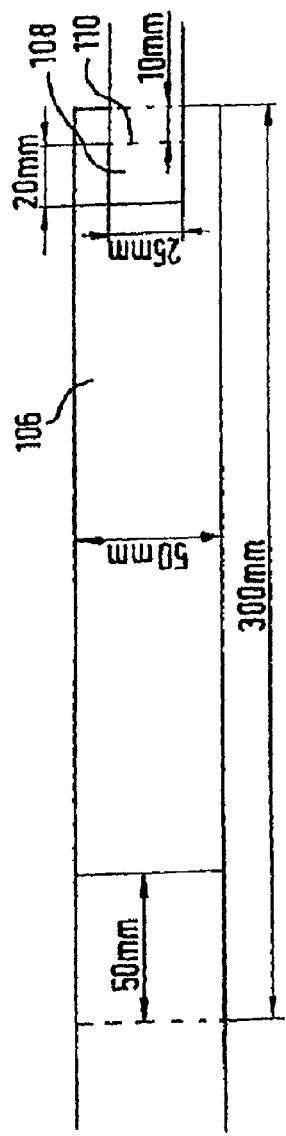
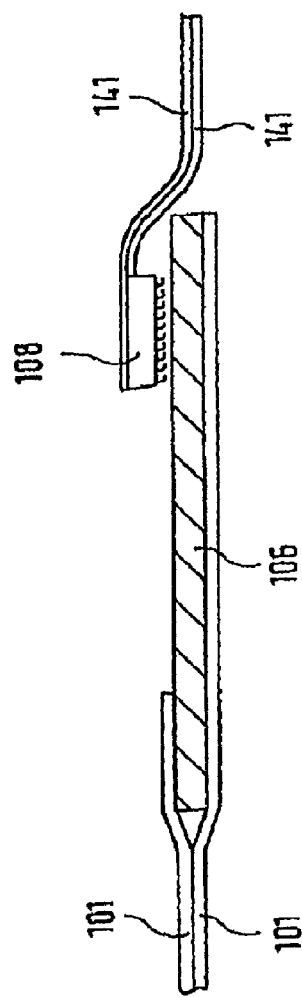
Fig. 9a
Fig. 9b

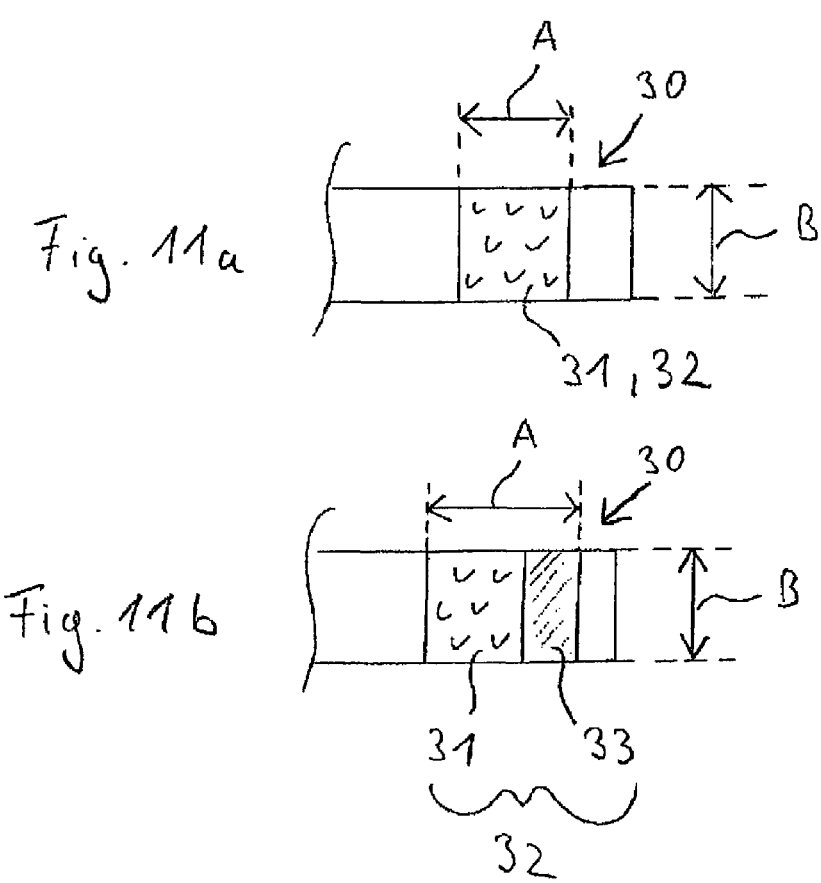

ABSORBENT INCONTINENCE ARTICLE WITH IMPROVED CLOSURE SYSTEM

This application is a continuation of U.S. Ser. No. 13/404,019 filed on Feb. 24, 2012, which is a continuation of U.S. Ser. No. 12/446,586 (now U.S. Pat. No. 8,152,788) filed Apr. 22, 2009 as the national stage of PCT/EP2007/009030 filed on Oct. 18, 2007 and claims Paris Convention Priority to EP 06 022 450.8 filed Oct. 27, 2006, the contents of each of which are incorporated by reference in their entirety. This application is also related to U.S. Ser. No. 13/798,242.

BACKGROUND OF THE INVENTION

The invention relates to an absorbent incontinence diaper with a rear area, a front area, and a crotch area lying between these, and with first and second side edges, and with a main part having an inner face directed toward the body and an outer face directed away from the body during use of the diaper, the main part comprising an absorption body and a backsheet on the side of the absorption body directed away from the body, the absorption body having a smaller width than the backsheet, and with discrete side parts joined to the first and second side edges. The incontinence article is intended for adults and is constituted as a disposable diaper, that is, intended to be used only once.

Such incontinence diapers are known, for example, from WO2004/105668A1.

In such incontinence diapers, the side parts can be made from a different material from that of the main part. For example, the side parts, which are also frequently referred to as the "ears" of the incontinence diaper, may be breathable, in particular, permeable to air and water vapor, whereas the main part, which is frequently termed the chassis, can be constituted so as to be impermeable to liquids, in particular, impermeable to moisture. To close the incontinence diaper, side parts non-detachably joined to the rear area are preferably wrapped onto the abdomen side of the user where they are detachably connected either to the outer face of the front area of the main part or to the outer face of the side parts of the front area.

If such an incontinence diaper is provided with mechanical closure aids, the problem results that, for the closure aids, which are usually constituted as hook-and-loop fasteners and are usually disposed on the rear side parts, a corresponding engagement surface must be provided on the outer face of the front area of the diaper that must be able to engage with the hooks of a hook-and-loop fastener.

However, the outer face of the main part of such incontinence diapers is usually constituted by a foil material to prevent the egress of liquid through the absorbent body to the outside. The side parts of such incontinence diapers are preferably made of smooth nonwoven materials to improve the diaper's gentleness to the skin in places where a secure barrier to liquid is not required. An engagement surface for secure attachment of the hooks of a hook-and-loop fastener on the outer face of the front area of the diaper would first require the attachment of an additional material, in particular, a known textile loop component. Such a loop component, however, would have to extend along a large part of the front area of the outer face of the diaper to guarantee the large degree of flexibility required for fitting incontinence diapers (diapers for adults). Because textile loop components are a considerable cost factor, such a solution is unacceptable for economic reasons alone.

Moreover, in the case of incontinence diapers of a known type, considerable differences in the subjectively perceived comfort of the diaper have been demonstrated despite side parts that are gentle to the skin and permeable to air and water vapor.

SUMMARY OF THE INVENTION

To solve these problems, it is suggested that the closure means having mechanical closure aids can, to correctly secure the diaper on the body of a user, be secured detachably at least in regions both on the outer face of the main part and also on the outer face of the side parts in the front area, the retaining forces between the mechanical closure means and the outer face of the main part being lower than the retaining forces between the mechanical closure means and the outer face of the side parts in the front area. The retaining forces are preferably determined as over-abdomen retaining forces.

The materials forming the outer face of the main part and the outer face of the side parts in the front area are inventively chosen so that, in addition to their primary function, they can also serve as the engagement surface for the closure means having mechanical closure aids. Surprisingly it has also been shown that, when the retaining forces between the closure means and the outer face of the main part are smaller than the retaining forces between the closure means and the outer face of the side parts in the front area of the diaper, the users of the diapers tend to close the diaper in such a way that the closure means are secured on the outer face of the side parts in the front area. This, in turn, increases the wearing comfort of the diaper because it avoids overlapping of the side parts with the backsheet, which enables the advantages of the permeability to air and water vapor of the side parts to take effect without obstruction. Moreover, the risk of damage to the backsheet of the main part and therefore the risk of liquid passing through the mechanical closure aids is reduced.

The essential characteristic is that the retaining forces between the outer face of the main part and the closure means having mechanical closure aids also help to hold the diaper on the body. For this purpose, it has proven advantageous if the over-abdomen retaining forces between the closure means and the outer face of the main part is 57-20 N/25 mm and, in particular, 50-25 N/25 mm.

Furthermore, the over-abdomen retaining forces between the closure means and the outer face of the side parts in the front area are preferably 90-58 N/mm and, in particular, 80-60 N/25 mm.

To determine the over-abdomen retaining forces, the closure of forces exerted during lateral strain are measured. A test method for determining the closure forces during lateral strain is given below:

To perform the test method, tensile test device of type Z010/TN 2S, strain gauge 100 N, obtainable from Zwick GmbH & Co KG, Ulm, Germany, can be used with a clamp jaw width of 60 mm for clamping the specimen. To perform the test method, the closure system to be tested with a loop component and a closure means having mechanical closure aids adhering thereto is placed on a curved surface, which is intended to simulate the curvature of the abdomen region of a user (see FIG. 8). To connect the closure components with the clamp jaws of the tensile test device, a flexible substrate, for example, an adhesive tape with adhesive properties on one side with a preferred width of 25 mm, or 50 mm is used (obtainable from 3M Deutschland GmbH, Neuss, Germany, with the designation STA 306). The adhesive tape is made of polypropylene and its surface is coated with a urethane-modified silicone polymer. The mass per unit area of the adhesive coating is 23 g/m². The specimen placed upon the curved surface, consisting of sections of the closure system forming areas adhering to one another, is subjected to tensile strain using the tensile test device, resulting in lateral strain on the sections forming areas adhering to one another.

Preparing the Sample:

The mechanical closure components to be used, that is, the material of the loop component 106 constituting the outer face of the front side parts of the main part and a closure means 108 of the closure system having mechanical closure aids, are conditioned at 23° C. and 50% relative air humidity for 24 h. As is described in more detail below, the loop component may, for example, be a nonwoven material or nonwoven-foil laminate. Specimens of size 50×300 mm are punched out of the loop component and fixed centrally sandwiched between two 50-mm wide one-sided adhesive tapes 101 with their adhesive surfaces facing each other in such a way that the lower adhesive tape covers the entire area of the rear side of the section and the upper adhesive tape overlaps the upper side (in the case of a nonwoven-foil laminate, the upper side is the nonwoven side) of the loop component over a length of 50 mm in such a way that the loop component protrudes 50×250 mm beyond the tape (see FIG. 9a, FIG. 9b). Similarly, the closure means 108 having mechanical closure aids is punched out over its entire length, that is, the same length as is to be used for the incontinence diaper, in the example 20 mm, and over a width of 25 mm, and is fixed using two 25-mm wide one-sided adhesive tapes 141 bonded to each other with their adhesive surface facing each other in such a way that the upper adhesive tape covers the entire area of the rear side of the section forming an area and the lower adhesive tape abuts the section forming an area (see FIG. 9a and FIG. 9b). The section forming an area of the closure means 108 having mechanical closure aids is now placed on the loop component 106, the distance from the longitudinal end edge of the loop component being 10 mm and that from each side longitudinal edge being 12.5 mm (see FIG. 9a). If the loop component 106 is available with a smaller dimension from the outset, so that it is not possible to provide a specimen measuring 50 mm×300 mm, the size of the specimen with a width of 25 mm and a certain length are selected and this section is fixed centrally sandwiched between the ends of two 25-mm wide one-sided adhesive tapes 101, as are described in more detail above, in such a way that the lower adhesive tape covers the entire area of the rear side of the section forming an area and the upper adhesive tape overlaps the loop component over such a length that the length of the loop component protruding beyond the tape is equal to the length of the section of the closure means 108 having mechanical closure aids (see FIG. 9c, FIG. 9d). In this case, the sections of the closure means 108 having mechanical closure aids and the loop component 106 prepared in this way are placed upon one another over their full area (FIG. 9c, FIG. 9d).

If no 25-mm wide section of the closure means 108 having mechanical closure aids is available, a correspondingly narrower section is used. In such cases, the forces determined are scaled with respect to a 25-mm wide section in such a way that the measured forces are multiplied by a factor f resulting from f=25/x, where x is the width of the specimen measured in mm.

The sections forming areas placed one upon the other in this way or in the way previously described are connected to each other by fourfold rolling with a 50-mm wide and 100-mm diameter roller with a smooth surface and roll weight of 5 kg, the rolling velocity being 20-100 mm/sec.

Test Method:

The loop component 106 extended as described above is clamped centered in the lower clamp jaws 122 of the tensile test device, and the opposite end of the closure means 108 having mechanical closure aids extended as described above is also clamped into the movable upper clamp jaws 123 of the tensile test device, also centered. The specimen thus clamped is placed over the test setup 100 shown in FIG. 8 and FIG. 10 intended to simulate the abdomen or hip region of the user. This test setup 100 is shown in a perspective view in FIG. 10. A surface 102 curved in a bow made of polished steel with a surface roughness of 5 to 25 mm and a radius of curvature R of 400 mm at least in sections and a cord length SL 300 mm are depicted. Moreover, above and below the curved surface 102, 18-mm diameter redirection rollers 104 are provided that redirect the specimen placed over the curved surface by H=88 mm in the vertical direction where it is then held in clamps 120, 124 of the tensile test device (not shown). The redirection is performed through an angle $\alpha$ of 60°. The pull-off angle is thus essentially tangential to the curved surface and kept constant. These sections 106, 108 forming areas placed one upon the other of the components of the closure means are positioned with respect to the curved surface 102 in such a way that the closure means having mechanical closure aids are centered in the center of the apex 5 of the curved surface 102. The movable clamp jaws 124 by which the closure means having mechanical closure aids are connected are moved in the direction of the arrow P at the test velocity stated below while the tensile force between the clamps is measured. The test parameters are:

Test velocity: 300/min

Clamping length of the specimen: 430 mm (see FIG. 8)

Measuring distance: distance until the components of the closure means separate

Initial force: 0.2 N

Number of test cycles: n≥6

Evaluation is performed in such a way that the maximum force measured before the closure means come apart rounded to 2 decimal places in N (Newtons) is recorded and stated as a mean value over n measurements.

For the mechanical closure aids, in particular, the hooks of a hook-and-loop fastener in the form known in prior art could be used. Preferably, a section having the hooks of the hook-and-loop fastener is laminated on the closure strip material by a known method. A closure strip is preferably anchored at one free end of the side part in question and itself has a free user end with the mechanical closure aids.

However, it is also conceivable and advantageous to provide multiple sections having the hooks of a hook-and-loop fastener at intervals on each of the closure strips. In this case, the closure strip exhibits low rigidity and can better adapt to the curvature of the body when the diaper is worn. The individual sections having the hooks of a hook-and-loop fastener preferably have a width, that is, an extent in the cross-direction of the diapers, of 1 to 10 mm and, in particular, 2 to 6 mm. The distance between the individual sections is, in particular, 0.1 to 3 mm, and further, in particular, 0.7 to 2 mm.

It is also conceivable and advantageous for the closure strip material to be elastically stretchable at least in regions.

Moreover, it is conceivable and advantageous, in addition to the mechanical closure aids constituted as mechanical elements, preferably the hooks of hook-and-loop fasteners, to provide adhesive closure aids, such as pressure-sensitive adhesive regions on the closure strips, to ensure even more reliable adhesion for the purpose of primary closure or, secondarily, for the purpose of disposing of the used diaper. The pressure-sensitive adhesive regions can, in particular, be provided in an outer region of the closure strip, that is, a region directly bordering the free end of the closure strip.

It is further conceivable for the closure means having mechanical closure aids to be anchored directly on the inner face of the side parts. In this case, the closure means would not be disposed on a closure strip extending beyond the free end of the side part but inside the side edge of the side parts.

In a preferred embodiment, the absorbent incontinent diaper has four discrete, not directly interconnected side parts such that one side part is attached to each of the two side edges of the front area and a further side part, to each of the two side edges of the rear area. In this case, the crotch area of the diaper lying between the front and rear side parts has no side parts, which improves air circulation of the diaper when it is applied. The crotch area of the diaper is also formed without incurring production waste (no leg cutout).

In an alternative embodiment, the incontinence diaper has only two discrete, not directly interconnected side parts such that a first side part is attached to the first side edge and a second side part is attached to the second side edge. In this case, it is advantageous if the first and second side part each extend continuously from the front area over the crotch area to the rear area. In particular, it proves advantageous with respect to economic production and in providing an attractive appearance of the diaper if the side parts end flush with the transverse ends of the main part.

At least in the front area, preferably also in the rear area, the side parts preferably have a nonwoven component, in particular, the side parts are constituted without any use of foil, further, in particular, the side parts consist of a one- or multi-layer non-woven component.

The outer face of the main part of the incontinence diaper is preferably, at least in regions, but, in particular, over its entire surface constituted by a nonwoven material. Nonwovens are considerably less expensive than textile loop components and are also particularly gentle to the skin. They also lend the incontinence diaper a textile-like appearance. In this case, it is advantageous for the backsheet of the main part to be made of a nonwoven-foil laminate, the nonwoven layer being outside and the foil layer being inside facing the absorbent body so that the nonwoven layer constitutes the outer face of the main part. This both ensures that the main part is impermeable to liquid and that the diaper is gentle to the skin.

The foil layer of this nonwoven-foil laminate is preferably made of a one- or multi-layer foil that is impermeable to liquid, but preferably also breathable. This has the advantage that the incontinence diaper is also breathable in the region of the main part.

All thermoplastic polymers can, in principle, be used as the materials for the foil. A large number of commercial products are available on the market. Preferably, LDPE (low-density polyethylene), LLDPE (linear low-density polyethylene), MDPE (medium-density polyethylene), HDPE (high-density polyethylene), and various PP (polypropylenes), and copolymers of ethylene or propylene are used combined with each other or with other comonomers. These polymers are used either in pure form or as polymer mixtures. Common ingredients for hygiene foils include mixtures of 10 to 90% by weight of LDPE, 10 to 90% by weight of LLDPE, and 0 to 50% of MDPE, for example, a mixture of 80% LDPE, 20% LLDPE and pigmentations suitable for the requirements.

Commercially available polymers for hygiene foils have the following melting point ranges or crystalline melting points:
LDPE=112 to 114° C.
LLDPE=119 to 125° C.
MDPE=125 to 128° C.
PP (block copolymers)=130 to 163° C.

Furthermore, ethylene vinyl acetate (EVA), ethylene acrylate (EA), ethylene ethyl acrylate (EEA), ethylene acrylic acid (EAA), ethylene methyl acrylate (EMA), ethylene butyl acrylate (EBA), polyester (PET), polyamid (PA), e.g. Nylon, ethylene vinyl alcohols (EVOH), polystyrene (PS), polyurethane (PU) and thermoplastic olefin elastomers are suitable as thermoplastic polymer materials for this foil.

As the material of the foil, polyolefins, such as LDPE, LLDPE, and PP are preferred. Mixtures of these polymers, for example, mixtures of LDPE and LLDPE, mixtures of LDPE or LLDPE and PP or mixtures of PE and PP with different melting points are especially preferred.

The foil is manufactured using a known method, for example, by blow extrusion or cast methods. In these methods, the expansions that the foil undergoes during extrusion are at least partially responsible for the foil's shrinkage during subsequent tempering (described in more detail below). Additional stretching is not necessary but, if desired, can be performed in a known way. In the case of breathable laminates, the provision of the breathability is preferably achieved by including a fine filling material in the mixture and stretching the foil or the composite material. Stretching causes microcracks in the foil that ensure the necessary permeability to water vapor and gas without impairing the water tightness to any considerable degree.

Numerous types of nonwovens can be used for the nonwoven components of the outer face of the main part and for the nonwoven component of the side parts in the front area, and preferably also in the rear area. In particular, all nonwovens are suitable that contain at least one initial component based on a thermoplastic polymer. The nonwovens can be fibers made of PE, PP, PET, Rayon, cellulose, PA, and mixtures of these fibers. Also bi- or multi-component fibers are conceivable and advantageous. In particular, carded nonwovens, spunbonded nonwovens, water-jet needle-punched nonwovens, SM nonwovens, SMS nonwovens, SMMS nonwovens or also laminates of one or more of these types of nonwovens are advantageous, where each S stands for a spunbond layer and each M for a meltblown nonwoven layer. Spunbond nonwovens are especially preferred because they possess high strength in the longitudinal and transverse direction and therefore withstand the lateral forces exerted on them due to the engagement of the mechanical closure aids especially well. To prevent fibers from being torn out of the nonwoven composite material when the mechanical closure aids are pulled apart, it is advantageous to provide the nonwoven component with an embossing pattern by means of which all fibers of the nonwoven component are preferably bound. In particular, a thermal embossing pattern is advantageously produced using calanders of the nonwoven material with the input of thermal energy.

The embossing pattern can include numerous spot-like joining points or joining regions in a known fashion and the joining points can have any conceivable geometric form. In particular, the joining points can be circular, oval, square, rectangular, rhombic, or star-shaped.

In an especially advantageous embodiment, the joining regions of the embossing pattern are disposed in such a way that the joining regions surround unconnected loop regions disposed in an island-like fashion. The joining regions can surround the loop regions continuously, that is, without gaps. However, it is also conceivable and advantageous for the joining regions to be formed, in particular, by smaller sections in the form of a line, that is, to provide the joining regions with gaps.

The geometrical shape of the unconnected loop regions disposed in an island-like fashion is in itself non-critical. The loop regions can be circular, oval, rectangular, square, triangular, hexagonal, octagonal, or have other polygonal shapes.

In particular, the joining regions can be constituted by numerous lines that intersect to form a regular rhombic pattern so that unconnected, rhombic loop regions disposed in an island-like fashion are surrounded by line-like joining regions. The closure means having mechanical closure aids can securely engage with these loop regions without a risk of fibers coming loose from the nonwoven component. Such an embossing pattern is disclosed, for example, in EP0882828A1.

A further preferred embossing pattern with loop regions disposed in an island-like fashion is disclosed in DE102004053469A1 which is hereby incorporated by reference. This embossing pattern corresponds to the previously mentioned joining regions provided with gaps.

The proportion of the area covered by the joining points or joining regions is preferably 7-40%, in particular, 15-30%, further, in particular, 17-25%.

The mass per unit area of the nonwoven component for the outer face of the main part is preferably 10-30 g/m$^2$, in particular, 14-25 g/m$^2$, further, in particular, 18-22 g/m$^2$.

The mass per unit area of the nonwoven component for the side parts is preferably 18-60 g/m$^2$, in particular, 25-45 g/m$^2$, further, in particular, 27-40 g/m$^2$ and further, in particular, 28-35 g/m$^2$.

The mass per unit area of the nonwoven component for the side parts in the front area and preferably also in the rear area is preferably greater than the mass per unit area of the nonwoven component for the outer face of the main part. Due to the higher mass per unit area of the nonwoven component for the side parts, a higher closure retaining force is possible because the mechanical closure aids can engage with more fiber material. The higher mass per unit area of the nonwoven component of the side parts also encourages the user to fix the closure means having mechanical closure aids preferably to the side parts and not to the outer face of the main part because the user associates greater reliability of closure with a higher mass per unit area and therefore preferably with a greater thickness of the nonwoven component. The nonwoven component of side parts therefore has a greater thickness than the nonwoven component of the outer part of the main part, the thickness being determined under a test pressure of 0.5 kPa.

In an especially preferred embodiment, the nonwoven components of the outer face of the main part of the side parts have the same embossing pattern. This is beneficial to the appearance of the hygiene article and the subjective perception of comfort by the user.

The nonwoven component of the outer face of the side parts in the front area, and preferably also in the rear area, is preferably constituted by a material that is permeable to water-based liquids. This improves the dissipation of perspiration from the inside to the outside.

In an especially preferred embodiment, the side parts in the front part and preferably also in the rear part consist essentially of a nonwoven component so that the outer face and also the inner face of the side parts largely comprise nonwoven components.

The outer face of nonwoven-foil laminate constituting the backsheet of an inventive incontinence diaper is intended to ensure an over-abdomen retaining force with the closure means having the mechanical closure aids that ensures secure attachment of the diaper to the body. For this purpose, it is advantageous, in addition to selecting suitable nonwoven and foil components, to use a suitable lamination method to produce the composite material made of a nonwoven and foil.

The lamination of the nonwoven component of the backsheet with the foil component of the backsheet can be performed by a known method by any joining methods, in particular, by gluing, embossing, ultrasonic welding, or thermocalandering. A preferred thermolamination method is disclosed in DE102004042405A1 and is hereby incorporated by reference.

It is also possible to produce the laminate by direct extrusion of the foil onto the nonwoven. Such composite materials are preferably subjected to a stretching step in at least one direction to increase the shrinkage that can be achieved in hot tempering (described in more detail below). Laminates in which the foil was connected to the nonwoven layer by direct extrusion are therefore embossed, stretched, in particular, by the known ring-rolling method, or preferably embossed and stretched.

Because many of the lamination methods for producing the nonwoven-foil laminates impair the plushness of the nonwoven component and therefore clearly reduce the over-abdomen retaining forces, it has proven advantageous to temperature-treat the nonwoven-foil laminate after lamination. This temperature-treatment results in the foil shrinking, in particular, by 1 to 10%, further, in particular, by 2-5%, in particular in the direction in which it previously was stretched during its production or during its lamination, that is, in the transverse and/or longitudinal direction. The shrinkage of the foil forces the nonwoven component connected to gather, resulting in an increase in mass per unit area, so that the nonwoven component can subsequently better engage with the closure means having mechanical closure aids and exhibits higher over-abdomen retaining forces than before temperature-treatment. Preferably temperature-treatment is performed by heating above the melting temperature of the foils. In such cases, the foil preferably has at least one component that has a lower melting point than at least one fiber component of the nonwoven component so that the fiber structure is not destroyed by the heating.

When referring to polymer materials in this present application, the melting point is the temperature at which the shear modulus of the material tends to zero. In the case of polymers with crystalline components or crystalline polymers, the crystalline regions will (also) have melted at this temperature.

When referring to a foil, the melting point is the temperature at which the foil melts as a whole. If the foil comprises more than one material, this does not require that every component in itself have a melting point at or below the melting point of the foil, but rather the melting point of the foil regularly corresponds to the temperature at which the main thermoplastic component melts. For example, a breathable foil containing 60% calcium carbonate, 32% of a polymer with a crystalline melting point of 138° C. and 8% of a polymer with a crystalline melting point of 158° C. has a melting point of approximately 138° C.

In the case of breathable foils, the breathability, for example, is mainly achieved by the addition of a fine filling material such as calcium carbonate, whose very high melting temperature essentially does not influence the melting point of the foil even with additives of over 50% by weight. For example, a foil made of a mixture of 60% calcium carbonate with 40% polymer has the same crystalline melting point as the polymer.

In the case of nonwovens comprising multiple material components, not all material components require a melting point above the temperature of the hot tempering, it is enough if at least one component has a higher melting point so that the integrity of the nonwoven is retained. It can even be advantageous if one material component of the nonwoven has a lower melting temperature because this can improve the composite adhesion of the laminate.

The preferred heating temperature-treatment of the nonwoven-foil laminate can be performed either directly after production (in-line) or later and independently thereof (off-line). The treatment is performed using a known method but the temperature must be set at least above the melting point of the main thermoplastic components of the foil in the nonwoven-foil laminate.

The process window of the heating is bounded at the lower end by the minimum temperature at which the foil is in the molten liquid state that is essential for hot tempering. The maximum temperature of the heating is determined by the crystalline melting point of the nonwoven web and, in the case of breathable foils, possibly also by a loss of breathability of the foil that may occur at excessive temperatures. If heating reaches the crystalline melting point of the nonwoven web, the good softness of the laminate is lost and there is a risk of pin-holes forming in the composite material. In the case of breathable foils, the hot tempering should be performed at temperatures at which the molten material is still too viscous to close the pores. Alternatively, the breathability can be produced after hot tempering, for example, by subjecting the composite material to ring-rolling after this step.

The hot tempering is preferably performed by heating the nonwoven-foil laminate by means of one or more hot rollers or alternatively, for example, by means of infrared radiation until the foil, that is, at least the raw material component of the foil with the lowest melting point, has reached the molten liquid state. After heating, the composite material passes directly to slow-running cooling rollers so that shock-cooling occurs and shrinkage between the heating element and cooling is possible due to the 1 to 10% lower circumferential velocity of the cooling rollers. The shrinkage should be in the range 1 to 10% (length/length) in the machine direction, shrinkage also occurs transverse to this, depending on the production and pretreatment of the foil. In the case of bubble foil, the transverse shrinkage is typically also 1 to 10%; for cast foils, it is typically lower. The temperature of the cooling rollers is preferably 10 to 30° C., so that the cooling of the composite material very quickly reaches a temperature below the melting point of the foil, e.g. within a fraction of a second.

Moreover, it has proven advantageous if the breathability of the side parts in the front area, and preferably also in the rear area, is greater than the breathability of the backsheet.

In an advantageous embodiment of the invention, the side parts in the front and/or rear area are folded open themselves about at least one folding line extending in the longitudinal direction. In particular, partial sections of the side parts folded on one another and lying against one another over an area in this folded configuration are detachably fixed to each other at joining points or in joining regions. This detachable fixture is preferably constituted by thermally or ultrasonically formed, preferably spot-shaped joining points. This has the advantage that the side parts can be reliably guided in fast-running production machines and also has advantages during removal from repackaging and preparation to apply the incontinence diapers. This makes the incontinence diaper easy to use and proves especially advantageous, in particular, for application by very infirm users.

In a further embodiment of this inventive principle, it proves advantageous if, in a partial section constituting the free end of the side part and folded in the transverse direction in this way, a grab region is provided for unfolding the material section. In the simplest case, this grab region can be constituted by a longitudinal side edge section of the stated part section which the user can grip using the fingers. It would also be conceivable for a separate manually grippable grab element to be provided on the partial section in question, which would, however, incur an additional manufacturing cost.

It proves especially advantageous if the detachable fixture to all joining points or joining regions can be detached by a single pull on the grab area of each side part. This simplifies handling and makes the incontinence diaper easier to use. In connection with the significance and testing of the feature of unfolding by single pulling, express reference is made to DE102004021353A1 and the test method disclosed therein which are hereby incorporated by reference.

In a further embodiment of this inventive principle, the side parts in the front area, and preferably also in the rear area, are folded upon themselves about at least two folding lines so that in cross-section a Z-shaped configuration is formed. In a further preferred embodiment, the side parts are folded upon themselves about three folding lines.

In a further preferred embodiment of the inventive incontinence diaper, the grab areas are facing outward before the side parts are unfolded in the front area, and preferably also in the rear area, in the cross-direction, that is, facing away from each other and from the longitudinal center axis of the main part of the diaper when it is spread out on a flat undersurface, so that they can comfortably be gripped with the left hand of a user from the left and with the right hand of the user from the right.

The extent of a side part joined to the main part beyond the side edge in the transverse direction in the unfolded state is preferably at least 10 cm, in particular, at least 15 cm, and further, in particular, at least 18 cm. It is preferably no more than 35 cm, in particular, no more than 30 cm and further, in particular, no more than 27 cm. The side parts joined to the main part have an extent in the longitudinal direction of the incontinence diaper in the area of joining to the main part of preferably at least 10 cm, in particular, at least 14 cm, in particular, at least 18 cm and further, in particular, at least 22 cm.

In a further embodiment of the invention, the side parts have (at least in the rear area) a reinforcing means that, viewed in the cross-direction, is narrower than each side part and that is provided at least in an area that bridges the side edge of the main part, that is, it extends both over a side edge area of the main part and over part of the side part in the transverse direction. This considerably increases the tear resistance of the side parts.

It proves especially advantageous if the reinforcing means extends essentially at least almost to a transverse edge of the side part facing the crotch area, that is, if it is flush with the transverse edge of the side part or even includes and surrounds the transverse edge.

The reinforcing means can extend in the longitudinal direction of the hygiene article, for example, over the entire longitudinal extent of the attached side part. It has been shown that this is not absolutely necessary but that it also proves advantageous if the reinforcing means has a smaller dimension in the longitudinal direction of the hygiene article than the attached side part itself. Because of the forces exerted during use on the side part and on the joining area of the side part and main part of the diaper, it is sufficient if the reinforcing means extends, for example, only up to 80% or, in particular, up to 60% and further, in particular, up to 50% of the longitudinal extent of the side part. This saves material compared with continuous reinforcement in the longitudinal direction.

The reinforcing means always extends beyond the side edge of the main part in the transverse direction toward the free end of the side part. This extending of the area of the reinforcing means beyond the side edge of the main part toward the free end of the side part, measured from the side edge of the main part, is preferably no more than 50%, in particular, no more than 35%, further, in particular, no more than 25%, further, in particular, no more than 20%, further, in particular, no more than 15%, further, in particular, no more than 10% of the transverse extent of the side part.

The reinforcing means also preferably extends in the transverse direction toward the longitudinal centerline of the main part so that it at least partially covers the region in which the side part and the materials of the main part overlap. The reinforcing means preferably extends over the entire overlapping region.

It proves highly advantageous if an attached side part can be constituted in the shape of a rectangle without the problem of tearing arising.

In a first embodiment of the invention, the inventively provided reinforcing means can be advantageously constituted by an attached reinforcing section, that is, by additional material added to the side part, in particular, applied on top of each side part. This reinforcing section can have any shape. This reinforcing section can, for example, also be constituted in the shape of a triangle.

This can be a section of a strip-shaped for ribbon-shaped material. In particular and advantageously, the reinforcing section can be constituted by a nonwoven material, textile material, or foil. Like the side parts, it can also be fed and attached in a continuous production process using the cut-and-place method.

If the reinforcing section is constituted by a nonwoven material and the reinforcing section is disposed on the outer face of the side parts, the outer face of the nonwoven material can preferably be engaged with the closure means having mechanical closure aids, for example, for the purpose of disposing of the used diaper.

The reinforcing section preferably has the same embossing pattern as the nonwoven material component of the side part and/or the outer face of the main part.

Multiple reinforcing sections can also be provided. The reinforcing means can be attached to one or both upper sides of the side part.

In an especially advantageous embodiment of the invention, the reinforcing means is constituted by the material of each side part itself by folding the side part once or multiply in the area overlapping the side area of the main part. In a top view of the hygiene article having just been unfolded, according to this embodiment, an area of each side part covering or overlapping the side edge of the main part is formed by double or multiple layers of material resulting from folding the side part. This provides especially effective protection against tearing. Folding of each side part in the shape of a Z, viewed in the longitudinal direction of the hygiene article, proves especially advantageous.

Further characteristics, details, and advantages of the invention result from the appended claims and from the drawings and the following description. Preferred embodiments of the inventive diaper in the drawing are shown by:

BRIEF DESCRIPTION OF THE DRAWING

FIGS. 11a, 11b top view of the user end of closing strips of an incontinence diaper

DESCRIPTION OF THE PREFERRED EMBODIMENT

Figure 1:
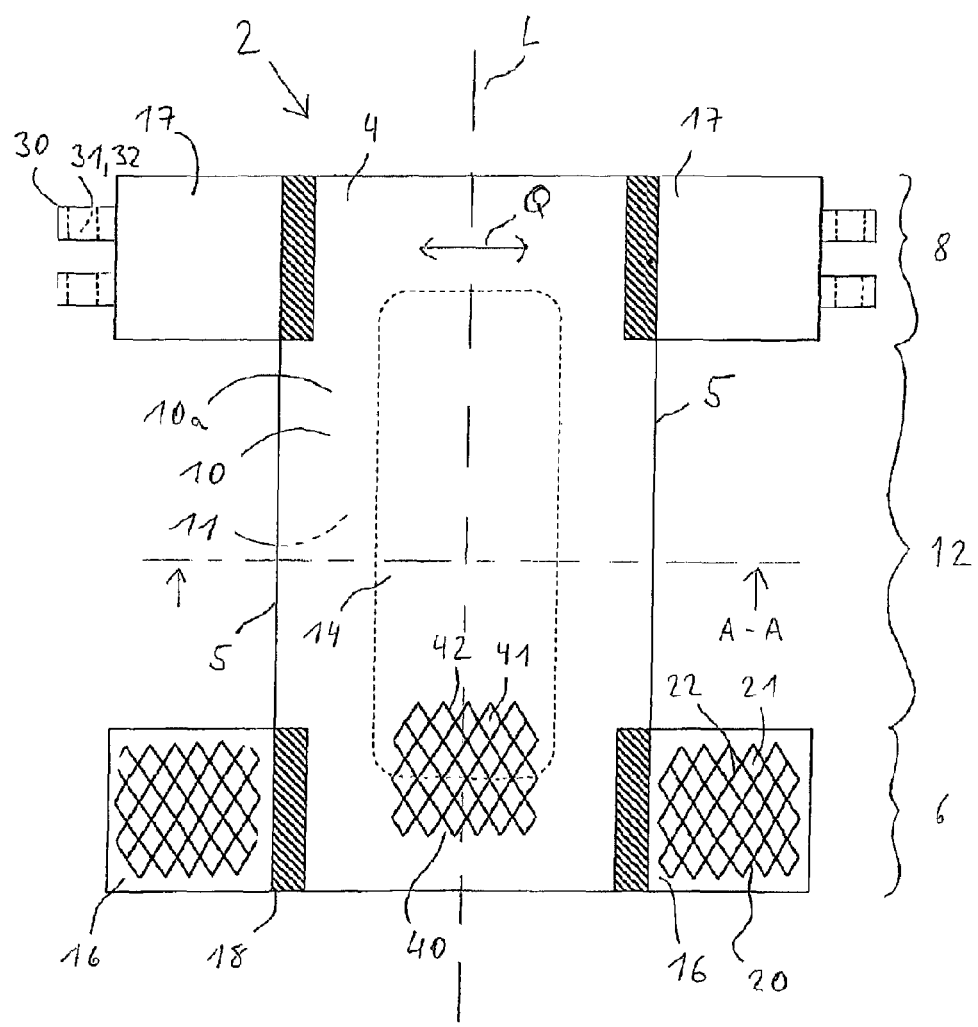
FIG. 1 a top view of the outer face of an inventive incontinence diaper

FIG. 1 shows a schematic top view of the outer face of an absorbent incontinence diaper 2 in a state of having just been unfolded. The incontinence diaper comprises a main part 4 with the longitudinal centerline L consisting of a front area 6, a rear area 8, and a crotch area 12 lying between the two in the longitudinal direction L. It also shows an absorbent body 14, which is usually disposed between the chassis-forming materials of the main part, that is, in particular, between a topsheet 11 that is permeable to liquids and a backsheet 10 of the main part 4 that is impermeable to liquids. However, embodiments are also conceivable in which the absorbent body can be applied to a chassis-forming layer of the main part as a separate unit provided with leakage protection and can be detachably or non-detachably fixed there.

Furthermore, the incontinence diaper 2 comprises front side parts 16 and rear side parts 17 that are attached to the main part 4 on both sides as separate nonwoven material components. They are each rectangular in shape, which is not essential, but is advantageous in terms of avoiding wasteful offcuts. The side parts are non-detachably connected in an overlap area 18 shown hatched with the chassis-forming materials of the main part 4, that is, for example, with the backsheet 10 and/or the topsheet 11 for use as intended. They extend beyond the lateral longitudinal edges 5 of the main part 4 in the transverse direction Q of the main part 4. The side parts 16, 17 are intended to be connected to each other when the incontinence diaper is applied to form a hip region of the hygiene article that is continuous in the circumferential direction. For this purpose, the side parts 16, 17 provided on one side of the main part are connected. This is achieved with closure means 32 having mechanical closure aids 31, in particular, hooks of a hook-and-loop fastener, of the closing strips 30 can be fixed on the outer face of the front side parts 16. FIG. 11a shows an enlarged top view of the user end of one of the closing strips 30 having a closure means 32 that is constituted only by the section of mechanical closure aids 31 in the form of hooks of a hook-and-loop fastener. The width B of the section of mechanical closure aids 31 is 25 mm in this case and its length A is 20 mm in this case. FIG. 11b shows an alternative embodiment of the user end of a closing strip 30 with a closure means 32 that is constituted by one section of mechanical closure aids 31 and one section of adhesive closure aids in the form of a pressure-sensitive adhesive region 33, the width B of the closure means 32 being 25 mm and the length A of the closure means 32 being 30 mm.

At least the front side parts 16, preferably also the rear side parts 17, are constituted by a nonwoven material component, in the case shown in the diagram, by a PP spunbond nonwoven with a mass per unit area of 30 g/m². The fiber thickness is 2 dtex. The outer face of the nonwoven material has an embossing pattern 20 that is only indicated schematically in FIG. 1. The joining regions produced by hot calender embossing are formed by a multiplicity of lines, that is, by two groups of lines extending parallel within each group, wherein the lines of one group intersect the lines of another group to form a regular rhombic pattern at an angle of 33° to produce unconnected rhombic loop regions 21 disposed in an island-like a fashion surrounded by line-like joining regions 22. The lines forming the joining regions 22 have a width of 1.0 mm in the case shown and an embossing depth of 0.6 mm. The distance between pairs of adjacent parallel lines of both groups of lines is 4.7 mm. The embossing area, that is, the sum of the area of all joining regions 22 with reference to the total area of the embossing pattern (joining regions+loop regions) is 32%.

The closure means 32 disposed on the inner face of the closing strips 30 of the rear side parts 17 can reliably engage with these loop regions 21 without any risk of fibers coming loose from the nonwoven component to an excessive degree.

Figure 2:
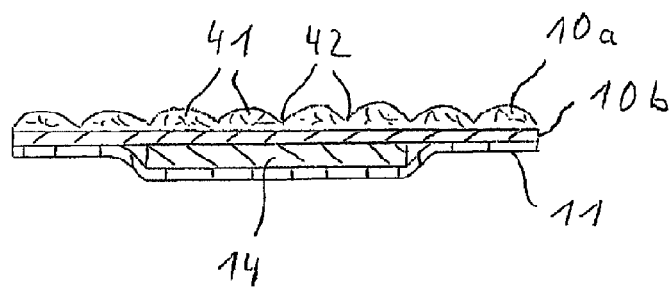
FIG. 2 cross-sectional view along a line A-A of the incontinence diaper shown in FIG. 1

The outer face of the backsheet 10 of the main part 4 is constituted by a backsheet nonwoven material component 10a. The diagram in FIG. 2 (not to scale) shows that the backsheet is formed from a nonwoven-foil laminate, that is, a backsheet foil component 10b is disposed between the absorbent body 14 and the backsheet nonwoven material component 10a. FIG. 2 also schematically shows the joining regions 42 and the loop regions 41 of the embossing pattern 40. In the case shown, the backsheet nonwoven material component 10a is also made of a PP spunbond nonwoven, but with a mass per unit area of 20 g/m². The fiber thickness is 2 dtex. The outer face of this spunbond nonwoven bears an embossing pattern 40, only indicated schematically in FIG. 1. In fact, the embossing pattern 40 extends over the entire outer face of the main part 4 from the front area 6, across the crotch area 12, to the rear area 8 of the incontinence diaper 2. The joining regions produced by hot calender embossing are constituted by a multiplicity of lines that mutually intersect to form a regular rhombic pattern so that unconnected rhombic loop regions 41 disposed in an island-like fashion are surrounded by line-like joining regions 42. In the case shown, the embossing pattern 40 of the backsheet nonwoven material component 10a is identical to the embossing pattern 20 of the nonwoven material component of the front side parts 16.

The over-abdomen retaining forces between the closure means 32 and the outer face of the side parts 16 are preferably at least 58 N/25 mm and are higher than the over-abdomen retaining forces between the closure means 32 and the outer face of the backsheet nonwoven material component, which are preferably at least 20 N/25 mm. This is essentially ensured by the higher mass per unit area of the nonwoven component of the side parts.

Figure 3:
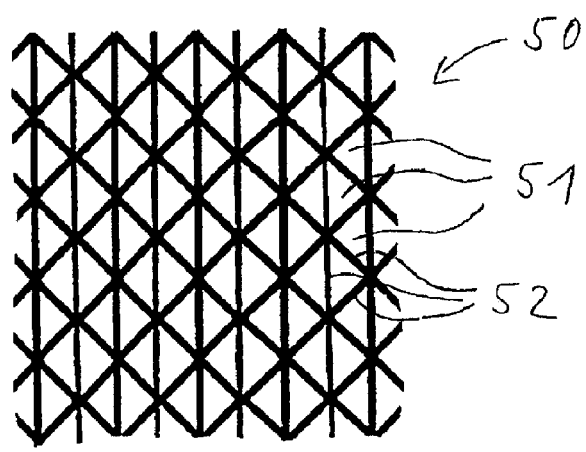
FIG. 3 an embossing pattern for a nonwoven material component

FIG. 3 schematically shows an alternative embossing pattern 50 produced by hot calandering for the nonwoven material components of the front side parts 16 and/or the backsheet 10. The embossing pattern 50 has joining regions that are formed by a multiplicity of lines and that mutually intersect to form a regular pattern so that unconnected triangular loop regions 51 disposed in an island-like a fashion are surrounded by line-like joining regions 52. The joining region, that is, the sum of the area of all joining regions 52 with reference to the total surface of the area of the nonwoven material covered by the embossing pattern 50 is 23% in this case.

Figure 4:
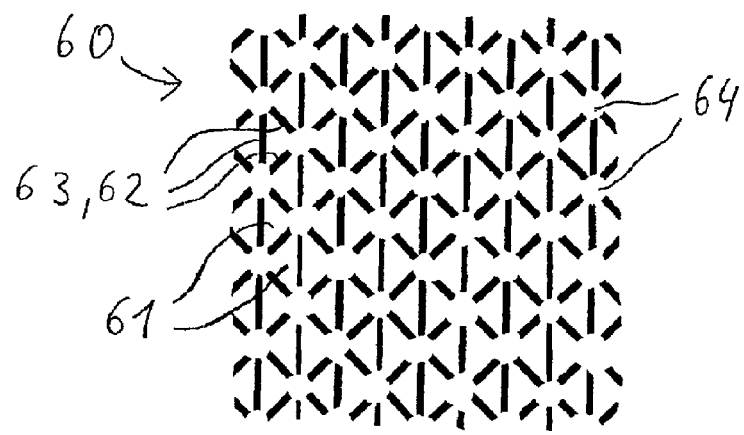
FIG. 4 a further embossing pattern for a nonwoven material component

FIG. 4 shows a schematic representation (not to scale) of a variant of the embossing pattern 50 shown in FIG. 3. In this case, the embossing pattern is an open embossing pattern 60. The joining regions 62 surround the triangular loop regions 61 discontinuously, that is with gaps, but the joining regions 62 are formed from a multiplicity of, in particular, smaller sections of line-like joining points 63 that do not intersect; the joining regions 62 are therefore provided with interruptions 64. This results in overall better tactile characteristics, in particular, in greater softness of a nonwoven material component provided with this embossing pattern 60. The line-like joining points 63 form the disconnected legs of a triangle. In a preferred embodiment of the open embossing pattern 60, the line-like joining points 63 have a length of 3 to 7 mm, in particular, 4 to 5 mm. The joining points 63 preferably have a uniform length so that they form a multiplicity of equilateral triangles. The width of the joining points 63 is preferably 0.2 to 0.8 mm, in particular, 0.4 to 0.6 mm. The embossing depth is preferably 0.2 to 1.0 mm, in particular, 0.4 to 0.8 mm. The embossing area, that is, the sum of the area of all joining regions 62 with reference to the total area of the region covered by the embossing pattern 60 is preferably 15 to 50%, in particular, 17 to 40%, further, in particular, 19 to 25%. In the case shown in FIG. 4, the embossing area is approximately 21%.

Figure 5:
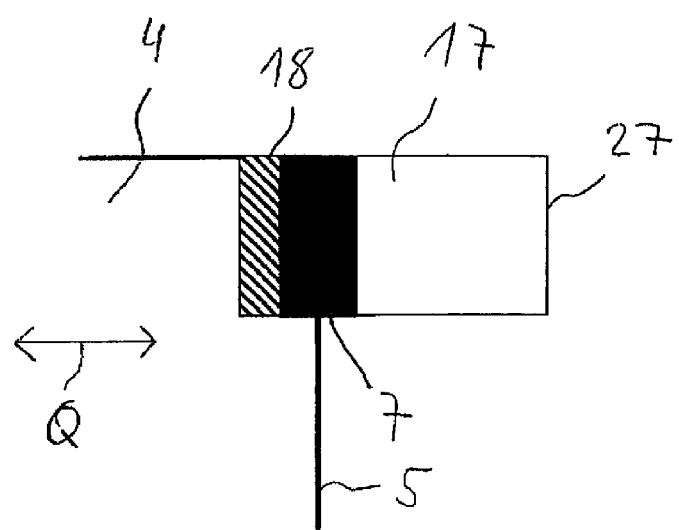
FIG. 5 a schematic representation of the joining of the side part to a main part with reinforcing means FIGS. 6 and 7 representations of hooks of a hook-and-loop fastener of a mechanical closing aid FIG. 8 schematic representation of the structure of a tensile test using a device with a curved surface FIGS. 9a, 9b, 9c, 9d schematic representations of the test object FIG. 10 perspective view of the device shown in FIG. 8

FIG. 5 shows a section of the rear area of an inventive embodiment of the incontinence diaper 2, wherein the schematically represented rear side part 17 has a reinforcing means 7 that is narrower than the side part 17 in the cross-direction Q. However, the reinforcing means 7 extends in the transverse direction Q beyond the side edge 5 of the main part 4. The reinforcing means 7 partially extends over the overlap region 18, as is shown schematically in FIG. 5. It therefore extends both over the lateral side edge 5 toward the free end 27 of the side part 17 and toward the overlap region 18, that is, toward a longitudinal centerline L of the main part 4.

The reinforcing means 7 can be constituted in different ways just as long as it provides tear protection for the side section 17, in particular, on application of a tensile force directed obliquely to the transverse direction Q on the side part 17 or the overlap area 18 on closure of the diaper by means of the closing strips 30 (not shown in FIG. 5). The reinforcing means 7 can, for example, be constituted by an additional reinforcing section, for example, nonwoven or foil, or by any material with reinforcement properties. This can be applied to the material of the side section 17 by any joining method, in particular, using an adhesive.

In a further embodiment not shown, the reinforcing means 7 is constituted by the material of the side part 17 itself by folding the side part 17 onto itself, in particular, in the shape of a Z, wherein the folded configuration extends beyond the side edge 5 of the main part 4 in the transverse direction Q toward the free end of the side part 17.

An especially preferred incontinence diaper 2 has the following components relevant to the over-abdomen retaining forces.

As Front Side Parts 16:

Material X: comprising 30-g/mm² polypropylene spunbond nonwoven, fiber thickness 2 dtex, hot calander embossing pattern on the outer face of the side part material according to FIG. 4, wherein the joining points 63 have a uniform length of 4.5 mm for a width of the joining points of 0.4 mm and for an embossing depth of 0.65 mm and an embossing area of 21.13%. The material can be obtained from Corovin GmbH Wohtorfer Str. 124, D-31201 Peine, Germany.

As Backsheet 10:

Material Y: A nonwoven-foil laminate was used that preferably forms the complete outer face of main part 4 of the incontinence diaper 2. The nonwoven material component comprises a 20-g/m² polypropylene spunbond nonwoven, fiber thickness 2 dtex, with a hot calander embossing pattern like that of the front side parts 16, that is, a hot calander embossing pattern according to FIG. 4, wherein the joining points 63 have a uniform length of 4.5 mm for a width of the joining points of 0.4 mm and an embossing depth of 0.65 mm and an embossing area of 21.13%, available from Corovin GmbH Wohtorfer Str. 124, D-31201 Peine, Germany. The foil component is a blow-extruded foil available from Rheinische Kunststoffwerke GmbH, Alkorstrasse 6, D-83512 Wasserburg, Germany. The foil is made using 70% low-melting-point polypropylene compound (melting point approx. 137 to 143° C.) and 30% high-melting-point polypropylene compound (melting point 158 to 164° C.). The compounds comprise a mixture of polymer raw material plus 60% $CaCO_3$ (chalk). After the blow extrusion of the precursor foil with a mass per unit area of 40 g/m², the foil was stretched in the machine direction using a mono axial MDO stretch device. In this way, the foil was stretched to a stretch ratio of 1:2 in the machine direction, that is, to a mass per unit area of 20 g/m² and therefore made breathable. The breathable foil was then thermolaminated at 130 to 140° C. together with the polypropylene spunbond nonwoven (20 g/m²) in a device such as is disclosed and described in FIG. 1 of DE102004042405A1. The nonwoven-foil laminate thus produced was then subjected to ring-rolling in the CD (transverse to the machine direction). This laminate was then subjected to hot tempering. The laminate passed through two hot rollers disposed one behind the other, whereby it was heated to a temperature above the melting point of the foil but below the melting point of the polypropylene spunbond nonwoven, that is, to 130 to 140° C. After the second hot roller, the laminate was directly fed to cooling rollers disposed one behind the other. These had a circumferential velocity lower than that of the heating rollers by an amount equivalent to the desired shrinkage in the machine direction, in this case approximately 5%.

As Closure Means 32 Having Mechanical Closure Aids 31

Figure 6:
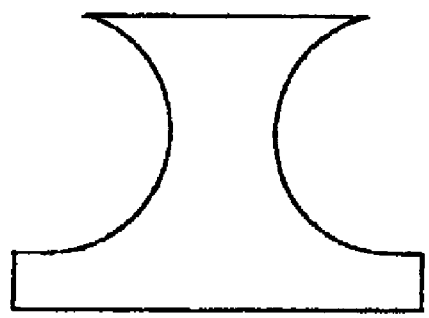
Figure 7:
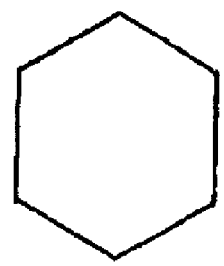
Figure 8:
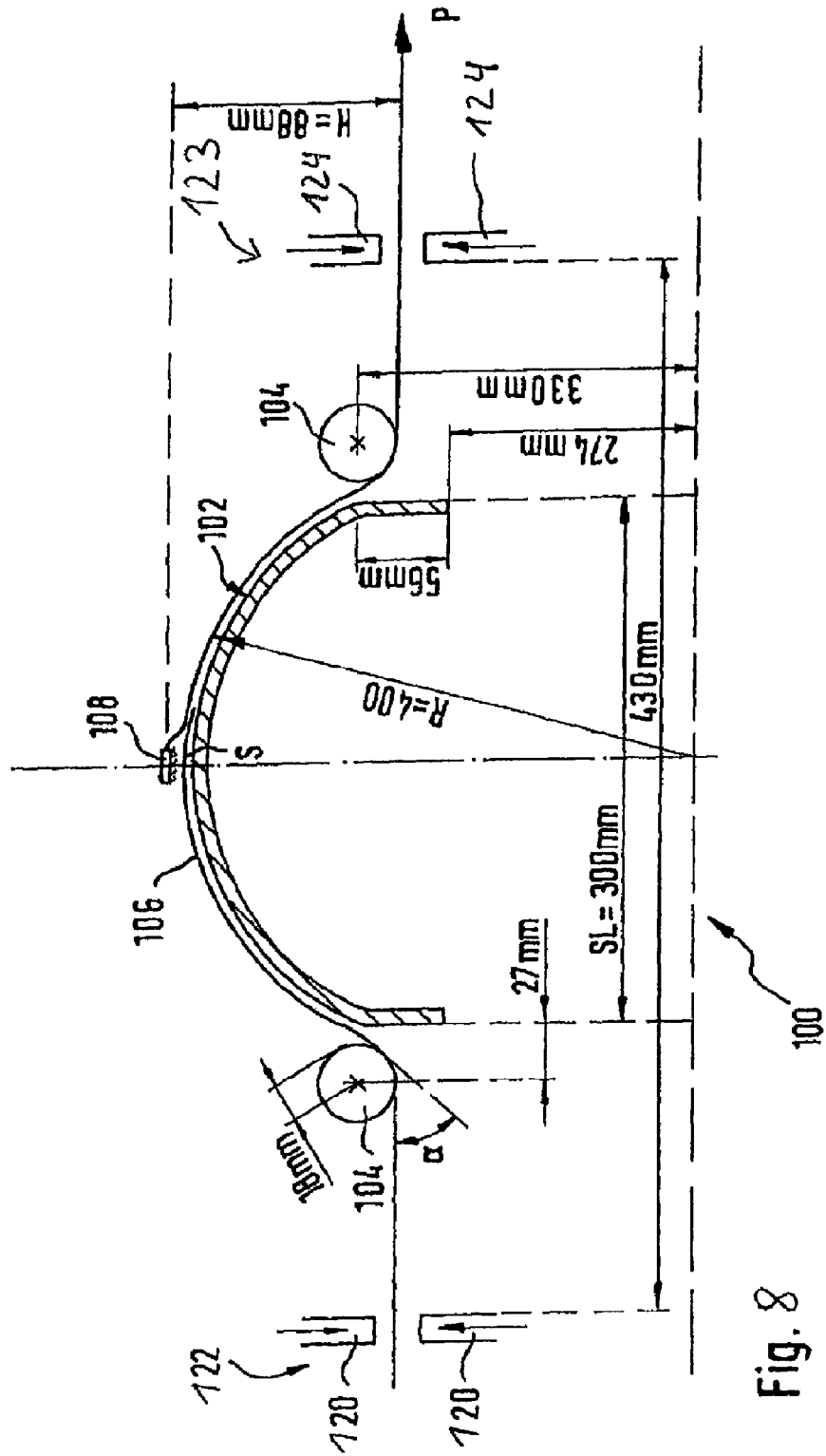
Figure 9C:
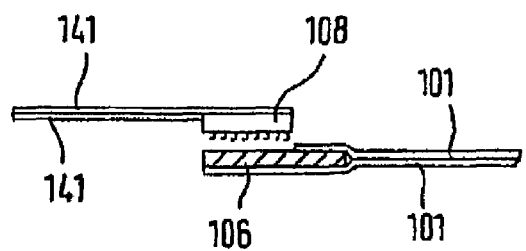
Figure 9D:
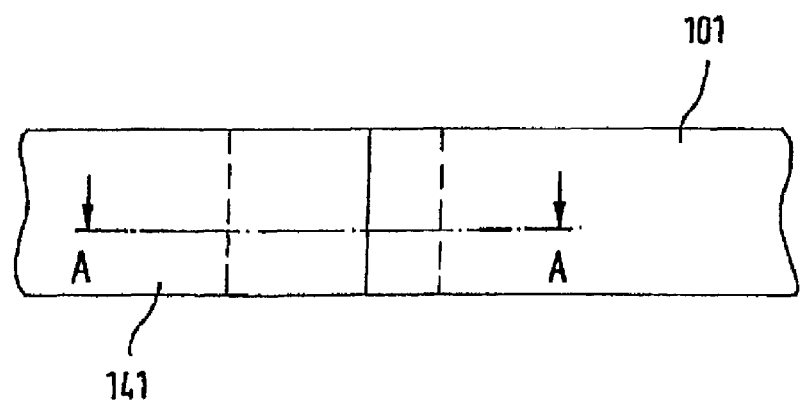
Figure 10:
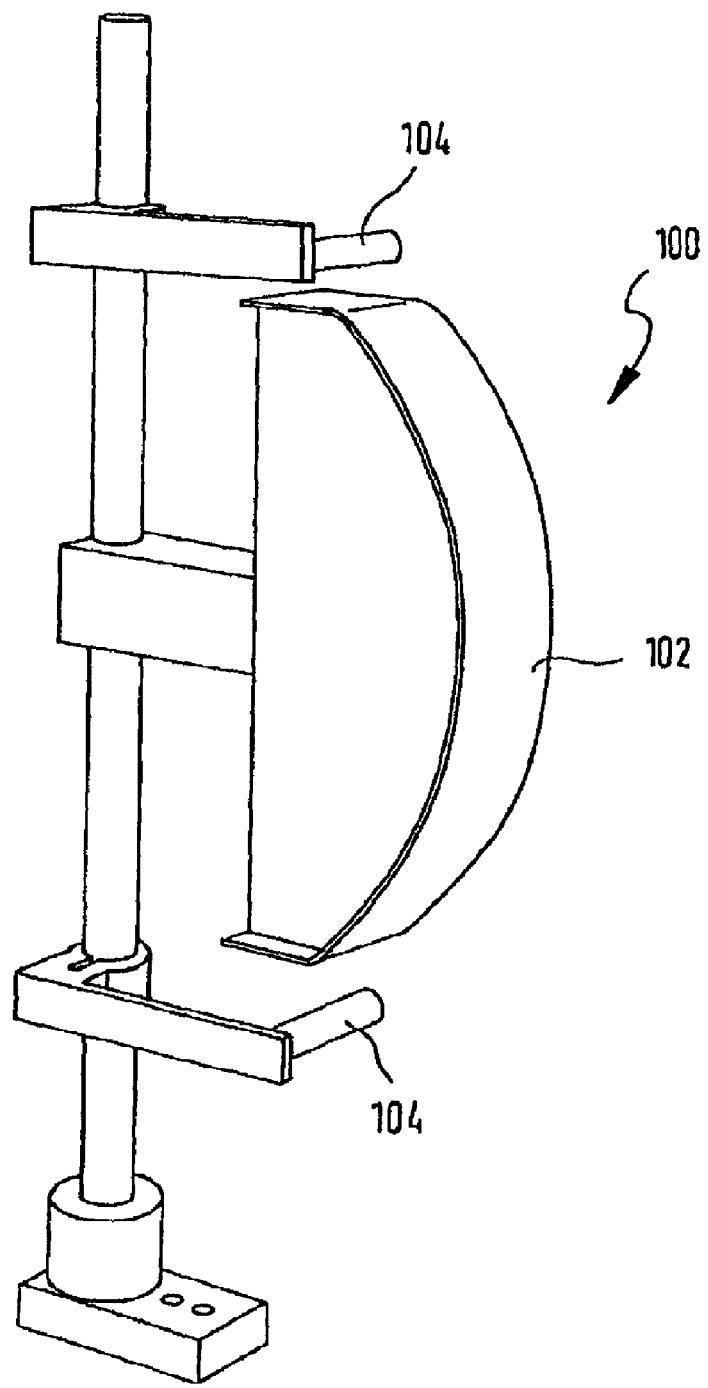

Material Z: section of hooks of a hook-and-loop fastener with dimensions 20×25 mm. Type Microplast® 42-288-HX200-PP3, item number 25445, available from G. Binder GmbH & Co KG Textil-und Kunststofftechnik, Holzgerlingen, Federal Republic of Germany. The representation of the shape of these hooks of a hook-and-loop fastener is shown in FIGS. 6 and 7. The hooks are mushroom-shaped (FIG. 6) with a hexagonal head surface 8 (FIG. 7). The hook density (number of hooks per unit area) is 288 hooks per cm². The material consists of polypropylene and has a thickness of 0.42 mm. It is manufactured by extrusion. The height of the mushroom-shaped protrusions over the base of the material is 0.26 mm. The distance between the edges of the hook heads is 200 µm.

The over-abdomen retaining forces of these materials determined as lateral forces according to the test method described above are as follows:

Outer face (embossing pattern side) of material X with material Z: 65.3 N/25 mm

Outer face (nonwoven material side) of material Y with material Z: 48.6 N/25 mm

The over-abdomen retaining forces of the closure means with the outer face of the side part material are therefore greater than the over-abdomen retaining forces of the closure means with the outer face of the nonwoven-foil laminate constituting the backsheet.

We claim:

1. An absorbent incontinence diaper for use on an adult user, comprising:
   a chassis comprising a liquid-permeable topsheet which, when in use on said adult user, is directed toward a user body and a liquid impermeable backsheet which, when in use on said adult user, is directed away from the user body, the backsheet having an outer face comprising a first nonwoven material having a first mass per unit area and having a first thickness;
   said chassis having:
     a front area which, when in use on said adult user, is located on a front of said adult user, said front area including a first front side and a second front side,
     a rear area which, when in use on said adult user, is located on a rear of said adult user, said rear area including a first rear side and a second rear side, and
     a crotch area located between the front area and the rear area;
   an absorbent body disposed between said liquid-permeable topsheet and said liquid impermeable backsheet;
   a pair of rear side parts, comprising
     a first discrete side part joined at said first rear side of said chassis, and
     a second discrete side part joined at said second rear side of said chassis;
   a pair of front side parts, comprising
     a third discrete side part joined at said first front side of said chassis, and having an outer face comprising a second nonwoven material, and
     a fourth discrete side part joined at said second front side of said chassis, and having an outer face comprising said second nonwoven material;
     said second nonwoven material has a second mass per unit area that is greater than said first mass per unit area of said first nonwoven material and has a second thickness which is greater than said first thickness of said first nonwoven material under a pressure of 0.5 kPa;
   a first closure aid, comprising a first mechanical closure aid, connected to said first discrete side part; said first closure aid configured for selective detachable fastening to said outer face of said backsheet and to said outer face of said third discrete side part;
   a second closure aid, comprising a second mechanical closure aid, connected to said second discrete side part; said second closure aid configured for selective detachable fastening to said outer face of said backsheet and to said outer face of said fourth discrete side part;
   wherein a retaining force between said first closure aid and said outer face of said backsheet when in use permits retention of said first closure aid for securing said diaper to said adult user and is lower than a retaining force between said first closure aid and said outer face of said third discrete side part; and
   wherein a retaining force between said second closure aid and said outer face of said backsheet when in use permits retention of said second closure aid for securing said diaper to said adult user and is lower than a retaining force between said second closure aid and said outer face of said fourth discrete side part.

2. The absorbent incontinence diaper of claim 1, wherein said backsheet comprises liquid impermeable material and said discrete side parts comprise liquid permeable material.

3. The absorbent incontinence diaper of claim 1, wherein said retaining force, determined as over-abdomen retaining force between said first closure aid and said outer face of said chassis, is between 57N/25 mm and 20 N/25 mm.

4. The absorbent incontinence diaper of claim 3, wherein said retaining force, determined as over-abdomen retaining force between said first closure aid and said outer face of said chassis is between 50N/25 and 25N/25 mm.

5. The absorbent incontinence diaper of claim 1, wherein said retaining force, determined as over-abdomen retaining force between said second closure aid and said outer face of said chassis, is between 57N/25 mm and 20 N/25 mm.

6. The absorbent incontinence diaper of claim 5, wherein said retaining force, determined as over-abdomen retaining force between said second closure aid and said outer face of said chassis, is between 50N/25 and 25N/25 mm.

7. The absorbent incontinence diaper of claim 1, wherein said first mechanical closure aid and said second mechanical closure aid comprise hooks of a hook-and-loop fastener.

8. The absorbent incontinence diaper of claim 7, wherein said first closure aid and said second closure aid further include an adhesive closure aid.

9. The absorbent incontinence diaper of claim 1, wherein a breathability of at least one of said pair of front side parts and said pair of rear side parts is greater than a breathability of said backsheet.

10. The absorbent incontinence diaper of claim 1, wherein said first discrete side part, said second discrete side part, said third discrete side part, and said fourth discrete side part extend beyond the chassis in a transverse direction in an unfolded state between 15 cm and 35 cm.

11. The absorbent incontinence diaper of claim 1, wherein said first discrete side part, said second discrete side part, said third discrete side part, and said fourth discrete side part extend along the chassis in a longitudinal direction at least 14 cm.

12. The absorbent incontinence diaper of claim 1, wherein said second mass per unit area of said second nonwoven material is 18-60 g/m².

13. The absorbent incontinence diaper of claim 12, wherein said second mass per unit area of said second nonwoven material is 25-45 g/m².

14. The absorbent incontinence diaper of claim 13, wherein said second mass per unit area of said second nonwoven material is 27-40 g/m².

15. The absorbent incontinence diaper of claim 1, wherein said first nonwoven material is provided with a first embossing pattern.

16. The absorbent incontinence diaper of claim 15, wherein said first embossing pattern is a thermal embossing pattern.

17. The absorbent incontinence diaper of claim 16, wherein said first embossing pattern includes joining points.

18. The absorbent incontinence diaper of claim 1, wherein said second nonwoven material is provided with a second embossing pattern.

19. The absorbent incontinence diaper of claim 18, wherein said second embossing pattern is a thermal embossing pattern.

20. The absorbent incontinence diaper of claim 19, wherein said second embossing pattern includes joining points.

21. An absorbent incontinence diaper for use on an adult user, comprising:
a chassis comprising a liquid-permeable topsheet which, when in use on said adult user, is directed toward a user body and a liquid impermeable backsheet which, when in use on said adult user, is directed away from the user body, the backsheet having an outer face comprising a first nonwoven material having a first mass per unit area and having a first thickness, said first nonwoven material is provided with a first thermal embossing pattern including joining points;
said chassis having:
a front area which, when in use on said adult user, is located on a front of said adult user, said front area including a first front side and a second front side,
a rear area which, when in use on said adult user, is located on a rear of said adult user, said rear area including a first rear side and a second rear side, and
a crotch area located between the front area and the rear area;
an absorbent body disposed between said liquid-permeable topsheet and said liquid impermeable backsheet;
a pair of rear side parts, comprising
a first discrete side part joined at said first rear side of said chassis, and
a second discrete side part joined at said second rear side of said chassis;
a pair of front side parts, comprising
a third discrete side part joined at said first front side of said chassis, and having an outer face comprising a second nonwoven material, and
a fourth discrete side part joined at said second front side of said chassis, and having an outer face comprising said second nonwoven material;
said second nonwoven material has a second mass per unit area, said second mass per unit area is 18-60 g/m² and is greater than said first mass per unit area of said first nonwoven material and has a second thickness which is greater than said first thickness of said first nonwoven material under a pressure of 0.5 kPa, said second nonwoven material having a second thermal embossing pattern including joining points;
a first closure aid, comprising first hooks of a hook-and-loop fastener and a first adhesive closure aid, connected to said first discrete side part; said first closure aid configured for selective detachable fastening to said outer face of said backsheet and to said outer face of said third discrete side part;
a second closure aid, comprising second hooks of a hook-and-loop fastener and a second adhesive closure aid, connected to said second discrete side part; said second closure aid configured for selective detachable fastening to said outer face of said backsheet and to said outer face of said fourth discrete side part;
wherein a retaining force between said first closure aid and said outer face of said backsheet when in use, is determined as over-abdomen retaining force, is between 57N/25 mm and 20 N/25 mm and is lower than a retaining force between said first closure aid and said outer face of said third discrete side part; and
wherein a retaining force between said second closure aid and said outer face of said backsheet when in use is determined as over-abdomen retaining force, is between 57N/25 mm and 20 N/25 mm and is lower than a retaining force between said second closure aid and said outer face of said fourth discrete side part.

* * * * *